United States Patent [19]

Gryaznov

[11] 3,950,447

[45] Apr. 13, 1976

[54] METHOD FOR CARRYING OUT SIMULTANEOUSLY THE CATALYTIC REACTIONS INVOLVING HYDROGEN EVOLUTION AND CONSUMPTION

[76] Inventor: Vladimir Mikhailovich Gryaznov, Leninskie Gory, MGU, zona L, kv. 11, Moscow, U.S.S.R.

[22] Filed: Apr. 30, 1971

[21] Appl. No.: 139,235

Related U.S. Application Data

[63] Continuation of Ser. No. 838,650, July 2, 1969, abandoned.

[52] U.S. Cl.......... 260/667; 260/683.3; 260/672 R; 260/680 R; 260/668 D; 260/666 P
[51] Int. Cl.$^2$.. C07C 5/10; C07C 3/00; C07C 15/00
[58] Field of Search ........ 260/666, 667, 669, 683.3; 55/16, 58; 48/224

[56] References Cited
UNITED STATES PATENTS

| | | | |
|---|---|---|---|
| 1,124,347 | 1/1915 | Snelling | 48/DIG. 4 |
| 1,174,631 | 3/1916 | Snelling | 55/16 |
| 1,685,759 | 9/1928 | Walter | 48/4 |
| 3,290,406 | 12/1966 | Pfefferle | 260/683.3 |
| 3,334,149 | 8/1967 | Akin et al. | 260/617 |
| 3,361,839 | 1/1968 | Lester | 260/669 |
| 3,375,288 | 3/1968 | De Rosset | 260/669 |
| 3,450,500 | 6/1969 | Setzer et al. | 23/212 |
| 3,476,818 | 11/1969 | Bunn, Jr. et al. | 260/667 |
| 3,562,346 | 2/1971 | Smirnov et al. | 260/683.3 |
| 3,779,711 | 12/1973 | Gryaznov et al. | 260/680 R |
| 3,849,076 | 11/1974 | Gryaznov et al. | 260/672 R |

OTHER PUBLICATIONS

A. A. Rodina et al., Zh. Fizkhim, 40(7), 1450–1456, (1966) – Chem. Abstracts 65:16082h 1966.

*Primary Examiner*—Delbert E. Gantz
*Assistant Examiner*—Juanita M. Nelson
*Attorney, Agent, or Firm*—Haseltine, Lake & Waters

[57] ABSTRACT

A method for carrying out simultaneously the catalytic reactions involving the evolution and consumption of hydrogen, which comprises conducting the reactions in a reaction space divided by a partition made from a material that is selectively permeable to hydrogen only and serves as a catalyst.

11 Claims, No Drawings

METHOD FOR CARRYING OUT SIMULTANEOUSLY THE CATALYTIC REACTIONS INVOLVING HYDROGEN EVOLUTION AND CONSUMPTION

This application is a continuation of Ser. No. 838,650, filed July 2, 1969 now abandoned.

This invention relates to catalytic processing of petroleum hydrocarbons, natural gases, vegetable oils and other raw materials and, more particularly, it relates to a method of simultaneously carrying out catalytic processes involving hydrogen evolution and consumption.

The present invention may find application for the manufacture of monomers to be used in the synthetic rubber, resin and plastic industries, for the production of detergents and pharmaceuticals, as well as for the manufacture of very pure hydrogen.

Known methods for the catalytic hydrogenation of unsaturated or aromatic compounds utilizing the hydrogen liberated as a result of carrying out the dehydrogenation of another compound require mixing the compounds participating in the dehydrogenation and hydrogenation reactions. This technique often makes the separation of target compounds from the reaction mixture excessively elaborate and, consequently, diminishes the profitability of the aforesaid combination of the dehydrogenation and hydrogenation processes.

It is likewise known to dehydrogenate hydrocarbons over a membrane catalyst consisting of palladium alloyed with 25 wt.% of silver, wherein the hydrogen evolved in the course of the reaction is subjected to oxidation on the other side of the membrane by oxygen diluted with nitrogen. This method makes it possible to dehydrogenate ethane to ethylene to the extent of 0.7 %. The latter method suffers from the drawback of providing no effective utilization of the hydrogen which has passed through the membrane and is noted for its high activity in hydrogenation reactions and for its high purity.

It is an object of the present invention to provide a method of simultaneously carrying out at least two reactions involving the evolution and consumption of hydrogen which will make it possible to avoid mixing the products of the reactions involving hydrogen splitting off and addition.

It is another object of the present invention to provide the utilization of active hydrogen liberated in the course of dehydrogenation reactions for carrying out the reactions of hydrogenation, hydrocracking, and, hydroisomerization or of other processes involving the addition of hydrogen.

It is a further object of the present invention to shift the thermodynamic equilibrium of the reaction towards higher yields of the target products.

It is still further object of the present invention to provide conditions for utilizing the heat evolved in the course of reactions involving the addition of hydrogen for accomplishing endothermic dehydrogenation reactions.

These objects have been accomplished by the provision of a method for simultaneously carrying out the reactions involving the evolution and consumption of hydrogen, wherein, according to the invention, the reactions are conducted in a reaction zone divided by a partition (membrane) consisting of a material which is selectively permeable to hydrogen only, and serves as a catalyst, so that on one side of the aforesaid partition hydrogen will be split off the feed stock, and the hydrogen thus evolved will penetrate through the partition to the other side thereof and will be combined with the compound fed to this reaction zone compartment and capable of undergoing hydrogen addition reactions. The process is carried out at 300°–500°C.

The material selectively permeable to hydrogen only may consists of palladium or palladium coated with a palladium black layer, or of palladium alloys.

A specific embodiment of the present method comprises carrying out on one side of the aforesaid partition the dehydrogenation of naphthenes accompanied by hydrogen evolution, and conducting on the other side of the aforesaid partition the hydrodealkylation of alkylaromatic hydrocarbons, with consumption of hydrogen which, on being evolved in the course of the dehydrogenation reaction, diffuses through the partition.

In another embodiment of the method, olefins are dehydrogenated on one side of the partition and the hydrogen thus evolved and allowed to diffuse through the partition is used on the other side of the partition for effecting the hydrogenation of aromatic hydrocarbons.

In a further embodiment of the method olefins are subjected to dehydrogenation on one side of the partition, while the hydrogen thus evolved and allowed to diffuse through the partition is used on the other side of the partition for carrying out the hydrodealkylation of alkylaromatic hydrocarbons.

The present method ensures continuous removal of hydrogen evolved during dehydrogenation, hydrogen being removed from the dehydrogenation zone due to its diffusion through a partition made from palladium or palladium alloy selectively permeable to hydrogen, and hydrogen consumption by a compound capable of undergoing a hydrogen addition reaction on the other side of the partition. Hydrogen removal from the dehydrogenation zone shifts the thermodynamic equilibrium towards higher target product yields, an added advantage of the method being associated with the fact that hydrogen diffusion through palladium results in the accumulation of highly active hydrogen on the other surface of the partition, and, therefore, provides for effective hydrodealkylation or hydrogenation of aromatic hydrocarbons.

For a better understanding of the present invention, the following examples are presented by way of illustration.

EXAMPLE I.

Simultaneous Dehydrogenation of Cyclohexane and Hydrodealkylation of o-Xylene.

The catalyst used comprises a palladium tube 300 mm long and having an outer diameter of 8 mm (wall thickness, 0.7 mm). On the outside, the tube is electrolytically coated with palladium black. Cyclohexane vapor is introduced into the tube, while the space between the tube walls and the reactor placed in a furnace is filled with o-xylene vapor. The hydrogen formed as a result of cyclohexane dehydrogenation diffuses through the walls of the palladium tube and is consumed in the demethylation of o-xylene. The pressure of hydrogen in each circuit of the apparatus is measured after freezing out the hydrocarbons, and hydrocarbon mixtures are analyzed by the chromatographic technique.

At a temperature of 430°C, the yield of benzene as a result of cyclohexane dehydrogenation equals 43%, while on the other side of the membrane catalyst the hydrodemethylation of o-xylene yields 6% of benzene. No toluene is detected in the products of o-xylene hydrodemethylation.

EXAMPLE 2.

Simultaneous Dehydrogenation of trans-Butene-2 and Hydrodealkylation of Toluene.

The catalyst used comprises a palladium tube 150 mm long and having an outside diameter of 3 mm (wall thickness, 0.1 mm). Inside the tube (1) is introduced toluene in an argon stream at a rate of 36 ml/min, the partial pressure of toluene being 92 mm Hg, whereas on the outside (II) the tube is surrounded with trans-butene-2 vapor fed at a rate of 2 ml/min and at atmospheric pressure. Listed in Table 1 is the yield of reaction products in the reaction spaces I and II depending upon the reaction temperature.

Table I

| Temperature, °C | Yield, % | | | | |
|---|---|---|---|---|---|
| | I | | | II | |
| | divinyl | cis-butene-2 | butene-1 | butene | benzene |
| 370 | 1.7 | 19.1 | 19.1 | 9.7 | 2.3 |
| 390 | 1.9 | — | 4.1 | 4.9 | 1.5 |
| 400 | 2.2 | — | 5.3 | 2.0 | 2.0 |
| 415 | 2.9 | — | 7.3 | 1.0 | 2.2 |
| 430 | 2.7 | — | 11.9 | 1.2 | 1.4 |
| 440 | 2.5 | 9.9 | 9.1 | 0.5 | 1.7 |
| 450 | 1.8 | 13.7 | 10.4 | 0.5 | 1.1 |
| 460 | 0.3 | 27.4 | 21.9 | 2.4 | 1.3 |

It follows from the data presented in Table I that the yield of divinyl in the temperature range of from 370° to 430°C is 2 to 3 times as that attainable under thermodynamic equilibrium conditions, so that hydrogen removal from the dehydrogenation zone through the palladium partition is conducive to enhanced target product yields.

EXAMPLE 3.

Simultaneous Dehydrogenation of trans-Butene-2 and Hydrogenation of Benzene

The catalyst used comprises a palladium tube 150 mm long and having an outside diameter of 3 mm (wall thickness, 0.1 mm). Inside the tube (reaction zone I) is fed trans-butene-2 vapor at a rate of 2 ml/min and under atmospheric pressure, while on the outside (reaction zone II) the tube is surrounded by benzene vapors in an argon stream at a rate of 3 ml/min, the partial pressure of benzene being 200 mm Hg. Table 2 lists the composition of the reaction products obtained in zones I and II. It follows from the data of Table 2 that combining of the processes of trans-butene-2 dehydrogenation to divinyl and of benzene hydrogenation to cyclohexane results in enhanced rates of both processes due to the diffusion of hydrogen from zone I to the other side (zone II) of the palladium tube where it emerges in a highly active state. Presented in Table 2 are the yields of dehydrogenation and hydrogenation products.

Table 2

| Reaction zone I | | Reaction zone II | |
|---|---|---|---|
| Temperature, °C | Yield of divinyl, % | Temperature, °C | Yield of cyclohexane % |
| 380 | 6.1 | 396 | 3.9 |
| 410 | 5.5 | 410 | 3.6 |
| 440 | 5.0 | 420 | 3.1 |
| 460 | 3.4 | 440 | 2.4 |
| | | 460 | 1.7 |

I claim:

1. A method for simultaneously carrying out a catalytic reaction wherein hydrogen is evolved and a catalytic reaction wherein hydrogen is consumed, said method comprising conducting each of said reactions in separate reaction zones isolated from one another by a membrane partition made of a catalytic material consisting essentially of palladium or alloys thereof and selectively permeable to hydrogen only, wherein in one reaction zone hydrogen is evolved from the material fed to said reaction zone, and wherein in the other reaction zone, the hydrogen is combined with the material fed to said other reaction zone, the hydrogen evolved in the first reaction zone passing through the partition which is selectively permeable thereto, said material being fed to the other reaction zone being capable of undergoing hydrogenation or hydrodealkylation, and maintaining the temperature in said reaction zones in the range of from 300° to 500°C to effect reaction in both zones, the palladium partition serving as the catalytic material in both zones.

2. A method according to claim 1, wherein the partition is made of palladium coated with palladium black.

3. A method according to claim 1, wherein the material from which hydrogen is evolved consists of naphthenes, and the material which adds hydrogen consists of aromatic hydrocarbons which are to be subjected to hydrodealkylation.

4. A method according to claim 1, wherein the material from which hydrogen is evolved consists of olefins, and the material which adds hydrogen consists of aromatic hydrocarbons which are to be subjected to hydrogenation or hydrodealkylation.

5. A method according to claim 3 wherein the material from which hydrogen is evolved is cyclohexane and the material which adds hydrogen is xylene.

6. A method according to claim 5 wherein the temperature is 430°C.

7. A method according to claim 4 wherein the material from which hydrogen is evolved is trans-butene-2 and the material which adds hydrogen is toluene.

8. A method according to claim 7 wherein the temperature is 370°–430°C.

9. A method according to claim 4 wherein the material from which hydrogen is evolved is trans-butene-2 and the material which adds hydrogen is benzene.

10. A method according to claim 9 wherein the temperature is 380°–410°C.

11. A method according to claim 1 wherein in said one reaction zone dehydrogenation of naphthenes or olefins is effected.

* * * * *